United States Patent [19]

Stone, Jr.

[11] Patent Number: 5,247,436
[45] Date of Patent: Sep. 21, 1993

[54] SYSTEM FOR INTERPOLATING SURFACE POTENTIAL VALUES FOR USE IN CALCULATING CURRENT DENSITY

[75] Inventor: Charles L. Stone, Jr., Darien, Conn.
[73] Assignee: Micro-Tek, Inc., Westport, Conn.
[21] Appl. No.: 763,862
[22] Filed: Sep. 20, 1991

Related U.S. Application Data

[63] Continuation of Ser. No. 382,622, Feb. 23, 1989, abandoned, which is a continuation-in-part of Ser. No. 85,971, Aug. 14, 1987, abandoned.

[51] Int. Cl.$^5$ .......................... G06F 15/42; A61B 5/04
[52] U.S. Cl. ................................ 364/413.05; 128/731
[58] Field of Search ..................... 364/413.05; 128/731

[56] References Cited

U.S. PATENT DOCUMENTS

| | | | |
|---|---|---|---|
| 4,416,288 | 11/1983 | Freeman | 128/731 |
| 4,498,080 | 2/1985 | Culver | 128/731 X |
| 4,736,751 | 4/1988 | Gevins et al. | 128/731 X |
| 4,744,029 | 5/1988 | Raviv et al. | 364/413.05 |

FOREIGN PATENT DOCUMENTS 8200633 11/1982 World Int. Prop. O.

OTHER PUBLICATIONS

Davis, Michael W. D. and David, Michael "Automatic Kriging and contouring in the presence of trends", J. Canadian Petroleum Technology, vol. 17, No. 1 Jan.--Mar. 1978.
G. Matheron "the Intrinsinc Random Functions and Their Applications", Advances in applied Probability, vol. 5, pp. 439-468 (1973).
B. D. Ripley "Spatial Statistics", in the series entitled Probalility and Mathematical Satistics Publ. by John Wiley, NY pp. 44-75 (1981).
R. L. Bras et al., "Random Functions and Hydrology", 1984, pp. 385-413, Addison-Wesley Publishing Co., Reading, MA., U.S.A.

*Primary Examiner*—Roy N. Envall, Jr.
*Assistant Examiner*—Andrew Bodendorf
*Attorney, Agent, or Firm*—Brumbaugh, Graves, Donohue & Raymond

[57] ABSTRACT

A system for mapping and/or displaying spatiotemporal features of underlying event-related neural activity involves measuring the event-related evoked potential values at a limited number of points over the region of interest, deriving a first grid of potential values at points over the area of interest representing at least about a five fold increase in the number of points by a Kriging-type of spatial statistical interpolation, and using the first grid to derive for the region of interest a second grid of points of current density values by a Laplacian conversion. A plurality of second grids of current density values spaced apart in time are derived and displayed on a monitor in cartoon-type fashion to provide a cartoon-type display of the features of the event-related evoked response over the region of interest varying with time. Various other displays are possible for highlighting specific features.

51 Claims, 2 Drawing Sheets

5,247,436

SYSTEM FOR INTERPOLATING SURFACE POTENTIAL VALUES FOR USE IN CALCULATING CURRENT DENSITY

This application is a continuation of application Ser. No. 07/382,622, filed on Feb. 23, 1989 now abandoned, which is a continuation-in-part of application Ser. No. 07/085,971, filed Aug. 14, 1987 now abandoned.

FIELD OF THE INVENTION

This invention relates to electrophysiological measuring techniques for deriving features of underlying neural activity in humans and animals.

The invention will be described more specifically with reference to the mapping and/or displaying of features of the current density at the surface of the human scalp in response to auditory stimuli although it will be apparent that the invention has broader application. In particular, the invention should similarly be applicable in cardiology, neurology and other situations where there is a practical limit to the number of probes or electrodes that can be used to study the current density of underlying neural activity.

The invention involves both processes and apparatus for doing the mapping and/or displaying.

BACKGROUND OF THE INVENTION

It has been known that cortical auditory evoked potentials (CAEP) elicited by speech sounds in humans generally exhibit characteristic waveshapes and scalp topography in response to specific acoustic features of the sounds, such as onset of voicing (VOT) and place of articulation. Electrophysiologic assessment of peripheral, brainstem and cortical responses to sound in young high-risk infants indicate that one or more levels of the auditory system may be involved in impaired auditory processing. Initial studies of language development in these infants also suggest that deviant cortical auditory processing in the young infant may be associated with poorer early language acquisition than infants with normal cortical responses to sound. So that possible remedial action may be taken as early as possible, early detection of impaired auditory processing is important.

To increase the usefulness of these electrophysiological measures, it is desirable to improve their specificity and sensitivity. To this end, for example, there is needed an improvement in techniques for the analysis of the pattern of auditory event related potentials (AERP) to speech and non-speech sounds.

It is known that the potentials recorded from the scalp derive from volume currents that originate in neuronal transmembrane currents within the brain. Active brain regions whose neurons are similarly oriented are capable of generating volume currents of sufficient magnitude to pass through the brain and its coverings, although markedly attenuated, where they are sensed as potential differences at the surface of the scalp. These volume currents must pass out of and back into the brain in order to complete the electrical circuit required by the conservation of charge. A good deal of the current flow within the scalp, however, is parallel to this surface rather than transcranial. Thus, the potential differences associated with lateral currents do not directly reflect transcranial flow and serve to diffuse the recorded potential distributions at the scalp surface. It has been suggested that the Laplacian derivation, which is proportional to the second spatial derivative of the field potential, is a measure of the current flow perpendicular to the recording surface, and therefore, of transcranial current flow. This measure provides a substantially more focused estimate of the intracranial sources of electrical activity than does the field potential distribution. It is also essentially reference independent, an important consideration in interpreting topographic data.

In practice it turns out that computation of the Laplacian requires a reasonably accurate estimate of the actual potential surface. It has been attempted to derive the Laplacian directly from the recording electrodes by a differential operator implemented by analog circuits in which the Laplacian at a particular point is derived as the average of the gradients from a number of surrounding recorded points. However, these direct analog attempts have not proven particularly successful in mapping an area because of the limited number of points available for use in the computation. In these attempts, the points used have been only the points directly measured and practical reasons limit the number of points that can be directly measured. In particular, the attempt to do such a Laplacian derivation directly with fifteen or twenty points, the limit generally thought practical to measure directly conveniently, has not proved satisfactory.

Similarly, in other electrophysiological processes involving the analysis of the pattern of neural potentials in both humans and animals, there can be used to advantage better techniques for mapping and/or displaying such potentials.

SUMMARY OF THE INVENTION

To this end, I have found that it is possible to use effectively in the Laplacian derivation interpolated points to supplement the directly measured points, and thereby to have enough points to do an effective Laplacian derivation. In particular, by use of a statistical spatial interpolation technique based on the probabilistic representation of regionalized variables, there is derived a grid of points that defines over the area under investigation, a relatively smoothly varying potential surface that passes through all of the measured points available with good support between points and of which the subsequent Laplacian derivation provides a surface of current density that is generally consistent with the surface expected and in which the display of features of interest is considerably improved. I have found it especially advantageous to use a modification of a statistical contour estimation method employed in non-physiological applications, primarily geological analysis, called "Kriging". This method has been developed to provide optimal estimates of large area contours sampled by discrete, often unsystematic point observations and its theory is described in a paper by G. Matheron entitled "The Intrinsic Random Functions and Their Applications" in Advances in Applied Probability, 1973, Vol. 5, pps. 439–468 and at pages 44–75 in a book by B. D. Ripley, entitled "Spatial Statistics" in the series entitled "Probability and Mathematical Statistics, published by John Wiley, New York; 1981. This Kriging method in its standard format has been programmed for use by a computer with various weighting procedures. For example, one form of Kriging software is commercially available from Golden Software of Golden, Colo. However, I have found that for use in electrophysiological processes of concern to the present invention, it is particularly advantageous to modify an ordinary Kriging treatment that uses for the estimation a linear polynomial to the 1.0 power (linear variogram), by using instead the same polynomial to a power of between 1.4 and 1.8 (power function variogram), and preferably 1.8. It is an advantage of this interpolation method that it appears to be useful for any particular electrode array and essentially independent of the particular distribution of the electrode array. Kriging of this kind has made possible transformation of a grid of fifteen points into a grid of almost fifteen hundred points.

The resulting three dimensional potential surface, in which the x and y coordinates correspond to the x and y coordinates of the point in a flattened plane simulating the surface of interest and the z coordinate is the potential value, normally exhibits a diffuse and rather featureless appearance. However, by use of a Laplacian transformation, for example, one involving a five point difference operator, there can be generated a three dimensional Laplacian surface in which discrete zones of outward (upgoing regions) and inward (downgoing) transcranial currents are clearly disclosed and are consistent with the results of more elaborate studies.

The five point difference operator serves as a discrete analogue to the Laplacian operator defined in multivariable calculus. This five point operator yields an output that approximates the second spatial derivative. It will be convenient hereinafter to refer to the output of a suitable discrete analogue of a Laplacian operator as an approximate second spatial derivative.

Summarizing, in an analysis in accordance with an illustrative embodiment of the invention, the topographic data will be subjected to a statistical spatial interpolation technique (e.g. Kriging) and then to two-dimensional current source density (Laplacian) analysis, so as to define the spatial distribution of transcranial current flow that occurs during the processing of auditory information in each task. Thereafter, the Laplacian data can be examined for spatially stable peaks that reflect circumscribed transcranial current flow associated with localized activation of specific cortical regions. The amplitude and timing of these peaks will be measured to define the locus, timing and magnitude of cortical activity associated with each task.

Moreover, because both Kriging and Laplacian transformation involve linear operators, it is feasible to combine mathematically both such operations in a single operation, although the subsequent discussion will be in terms of separate operations.

Moreover, for ease of interpretation, in a preferred embodiment my invention further includes the conversion of each derived set of x, y, z data points into a three dimensional perspective image that directly displays the profile of the variable of interest as height above the electrode grid on the scalp surface. Moreover, by displaying successive frames displaced in time in cartoon-display fashion, there can be displayed in three-dimensions the continuous evolution of the Laplacian surface over the real- time auditory evoked potential period being measured.

Additionally, to facilitate comparison of an individual case with a grand mean of representative normal cases and with a z- score transformation of the case data, the moving three dimensional Laplacian surface generated for an individual case is displayed in one window of a three window monitor screen, the corresponding surface for the grand mean in a second window, and the z-score of the comparison in a third window.

Additionally, there may be displayed the Laplacian value of any point including any original measuring point as it varies with time.

The invention will be better understood from the following more detailed description taken with the accompanying drawings.

DETAILED DESCRIPTION OF THE INVENTION

Figure 1:
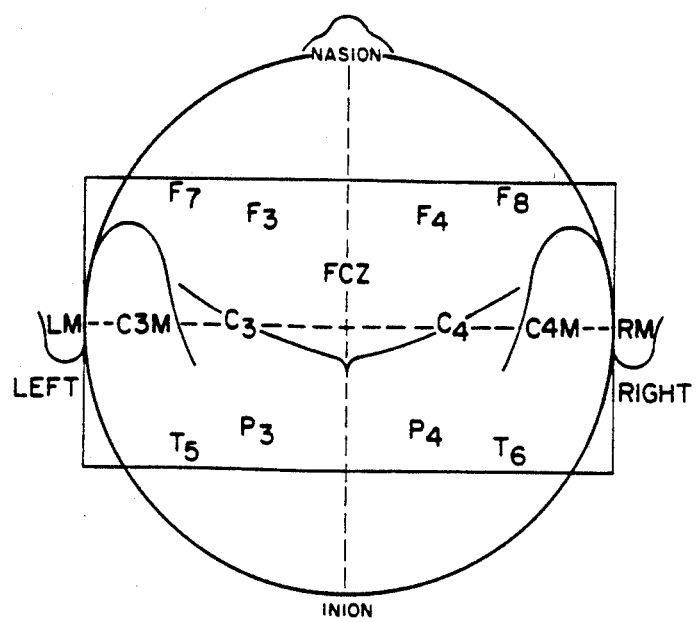
FIG. 1 shows the outline of a head and the disposition of fifteen electrodes over the head for collection of the electrophysiological data, for further processing in accordance with the invention.

Before beginning the detailed description, some additional background will be helpful.

As is known, two basic problems confront the interpretation of the topography of event-related potentials. First, two electrodes, an "active" and a "reference" are required in bioelectrode recordings. Scalp electrode sites are rarely inactive with respect to intracranially generated potentials, and even noncephalic sites are not inactive with respect to potentials generated within the auditory system, due to the vertical orientation of the active generators of auditory evoked potentials. Therefore, potentials recorded from most scalp loci contain contributions from both the active and reference electrodes, so absolute potential values are not generally obtainable. Identification of the intracranial generators of an observed potential distribution is further complicated by the effects of the shape and impedance characteristics of the brain and its coverings. The volume conduction characteristics of the head lead to an extensive diffusion of currents that result in broadly distributed field potentials at the surface of the scalp. Thus, it is often difficult to differentiate potentials generated even within widely spaced intracranial structures due to their extensive spatial overlap at the scalp. These same considerations persist when there is measured a potential distribution at the surface of a human or animals essentially anywhere along the surface.

The reference problem is generally solved by describing the surface topography in terms of potential gradients, usually defined empirically as the potential differences between adjacent scalp electrodes. Since the reference is common to both electrode linkages, any contribution it might make to the potentials recorded at each site is canceled. However, this does nothing to reduce the broad scalp potential distribution due to volume current spread. It has previously been proposed that the component of volume current that flows laterally within the scalp itself can be eliminated by the use of a two dimensional current source density (Laplacian)

method. This technique eliminates contributions to the surface potential distribution from tangential current flow, yielding an estimate of the transcranial currents alone. Empirically, this method provides a striking sharpening of the observed electric events.

It is possible to obtain a crude estimate of the Laplacian distribution using analog combinations of the observed potential values at each electrode. However, in implementing Laplacian analyses using a five point differential operator, it is found that close point spacings are needed to adequately estimate the second spatial derivative when based directly on interelectrode gradients. Since optimally dense arrays require too many electrodes to be generally practical, I have sought methods for accurate interpolation of the observed potential values between electrodes so the Laplacian could be calculated using the interpolated voltages. Since the surface potential gradients are affected by generator size and depth, there is no fixed formula for accurate interpolation. Specifically, linear and inverse distance squared interpolations commonly used in mapping applications tend not to fit accurately observed physiological surface distributions. Additionally, various other interpolation techniques such as splining have proved relatively ineffective in providing meaningful results. Accordingly, in accordance with an illustrative embodiment of the invention, as mentioned earlier, there is advantageously employed a statistical contour estimation method employed previously only in non-physiological applications, i.e., geologic and geographic analyses. Specifically, the method called "Kriging", referenced above, has been developed to provide optimal estimates, based on a global rather than local fit, of large area contours sampled by discrete, often unsystematic, widely spaced point observations. In particular, I have used Kriging to estimate a relatively dense rectangular grid of potential values that is a numerical representation of a three dimensional potential surface of a relatively small scale. The grid is a numerical matrix whose elements are measurements of the Z variable made at points identified by the two rectangular planar coordinates X and Y. This grid of voltage values in turn is used in the Laplacian derivation to provide a similarly dense rectangular grid of current density values that is a numerical representation of the current density surface of primary interest.

Although this method will not correct failures to sample major features of the original ERP field distribution because they occur between electrode positions, Kriging can provide very satisfactory representation of ERP amplitude contours, with satisfactorily convenient electrode density.

Kriging has been used in the geosciences to estimate values of a large area surface at the nodes of a rectangular grid from irregularly widely spaced sample data points. Kriging involves a number of levels, two of which, universal and ordinary Kriging, are most relevant for my invention. Ordinary Kriging will be discussed more fully below in connection with an exemplary embodiment. Of possible interest also is the more general universal Kriging. Universal Kriging makes optimal use of autocorrelation between points on a surface and like ordinary Kriging requires an approximation of the spatial autocorrelation between sample data points before contouring is begun. As will appear below, the difference is that ordinary Kriging assumes the absence of any fixed trend underlying the data whereas universal Kriging incorporates a fixed, or deterministic, underlying trend. In other words, ordinary Kriging is universal Kriging in which the trend model is not a polynomial or some other higher order function, rather, the underlying trend is a constant, i.e., a flat plane. The universal Kriging option will be more appropriate when denser electrode arrays are used, and/or a better understanding of the actual underlying neural activity is available.

Each of these forms of Kriging involves the use of a variogram, which is a function relating the covariance of the difference between points, to the distance between the points and an important parameter to be selected is the form and the order of the variogram.

As discussed more fully in a paper entitled "Automatic Kriging and contouring in the presence of trends (Universal Kriging Made Simple)" published in the Journal of Canadian Petroleum Technology by M. W. D. Davis and M. David, Vol. 17, No. 1 January-March, 1978, the role of Kriging is defined as follows. Given a series of values $Z(x_i)$ known at a series of points $x_1, x_2, \ldots x_n$, what are the best weights $\lambda_1, \lambda_2, \ldots \lambda_n$ to be applied to the known values in order to obtain the estimated value $\hat{Z}(x)$, i.e. the interpolated value desired, at any point x where the information is desired, $$\hat{Z}(x) = \sum_{i=1}^{N} \lambda_i Z(x_i).$$

A usually accepted criteria of goodness of fit is the sum of squared differences between the real and the estimated values. The geostatiscal theory of Matheron allows the calculation of this sum of squares (variance of the estimation error) as a function of the data points only, plus a model. This model is to consider the phenomenon under study as one realization of a random process in the plane.

Conceptually, let us divide the surface Z (x) into a trend and a fluctuation $$Z(x) = m(x) + \epsilon(x).$$

where trend m is a large - scale variation regarded as fixed, and the fluctuation $\epsilon$ is a small-scale random process. We will assume that the covariance function C (x, y) is known, and no stationarity condition is needed, as will be discussed more fully below. The C is the covariance function of $\epsilon$ as well as of Z.

The importance of the above formula is that the two components are predicted separately. For a smooth summary, there is used $$\bar{Z}(x) = \hat{m}(x)$$

whereas for interpolation $$\hat{Z}(x) = \hat{m}(x) + \hat{\epsilon}(x)$$

where "^" indicated a predicted value and "-" is the approximation symbol.

A first condition added to the model is that the random function be homogeneous i.e. there is no systematic trend in the distribution, also known as stationarity. Then it is possible to define a variogram of the phenomenon and to express the variance of the estimation error as a function of this variogram. Having an expression for the variance, it is possible to minimize it with respect to the weighting coefficients used at each point. This is usually defined as ordinary Kriging, a variation of which is involved in my presently preferred form of the invention.

However, further enhancement of the desired characteristics may be achieved by universal Kriging in which the variogram and the trend are more closely fitted to the known characteristics of the data by selection of mathematical expressions for these terms which incorporate what is known about the underlying neural activity.

There now will be developed the ordinary Kriging equations for the optimal weights, $\lambda_i$ and the minimum mean square error; given that the covariance, cov(v) is known and the mean is assumed to be constant, where $v = u_1 - u_2$, i.e., the difference between the points $u_1$ and $u_2$.

The mean square error of estimation or estimation variance equation is given by $$\sigma_p^2 = \frac{1}{A^2} \int_A \int_A cov(u_1 - u_2) \, du_1 du_2 -$$

$$\frac{2}{A} \int_A \sum_{i=1}^{n} \lambda_1 cov(u - u_1) du + \sum_{i=1}^{n} \sum_{j=1}^{n} \lambda_i \lambda_j cov(u_i - u_j).$$

To find the set of weights that give the minimum mean square error (MSE), the expression on the right of the above equation must be minimized subject to the constraint that all the weights add to 1 (unbiased)

This set of weights is given by solving the following set of (n+1) linear equations in n weights $\lambda 1$, and the Lagrange multiplier $\mu$.

$$\sum_{j=1}^{n} \lambda_j cov(u_i - u_j) + \mu = \frac{1}{A} \int_A cov(u - u_i) du \quad i = 1, 2, \ldots, n.$$

$$\sum_{i=1}^{n} \lambda_i = 1$$

The solution gives the optimal weights which will be denoted $\lambda_i^*$.

The minimum MSE, $\sigma_p^{2*}$ is derived to be $$\sigma_p^{2*} = \frac{1}{A^2} \int_A \int_A cov(u_1 - u_2) \, du_1 du_2 -$$

$$\frac{1}{A} \int_A \sum_{i=1}^{n} \lambda_1^* cov(u - u_i) du - \mu.$$

An important element of this approach is the selection of an appropriate variogram to model the known spatial characteristics of the phenomenon being investigated. The variogram is generally described as follows. Consider two real numerical values Z(x) and Z(x+h) at two points x and (x+h) separated by the vector h. The variability between these two quantities is characterized by the variogram function $2\gamma(x,h)$, which is defined as the expectation (E), or mean, of the random variable $[Z(x) - Z(x+h)]^2$, i.e. $2\gamma(x,h) = E\{[Z(x) - Z(x+h)]^2\}$. This model should be one that yields results consistent with results known to be accurate based on earlier experience. This generally requires that the variogram model chosen be one which provides parabolic behavior of the variogram at small separation distances and whose parameters yield a surface which passes smoothly through all the data points with maximum support between the data points.

A variogram model found to satisfy these requirements for the situation under study is $$\gamma(h) = wh^b$$

where the slope (w) is one and the exponent (b) is chosen appropriately. As previously mentioned, programs for carrying out ordinary Kriging in which the exponent value (b) above is one, are commercially available, e.g. Golden Software.

I have found that it is particularly advantageous in the embodiments of my invention being described to use ordinary Kriging in which the variogram model uses a value of (b) between 1.4 and 1.8, and most advantageously 1.8.

In the above set of ordinary Kriging equations the chosen variogram with the appropriate parameter values can be substituted into the estimation variance equation for the term $cov(u_i - u_2)$ to obtain the desired results.

A specific example, in accordance with the above treatment, of ordinary Kriging using the specific variogram model set forth above, for the preferred value of 1.8 as the power of the power function, follows.

A set of 15 electrodes, as seen in FIG. 1, is used to derive, at a given instant in time, an interpolated surface of potential values.

The interpolated surface is defined by a regular grid of points; this grid has 23 rows by 63 columns for a total of 1,449. A value at each and every grid point is computed as a weighted average of the 15 electrode measurements available:

$$\hat{Z}_k = \sum_{i=1}^{15} \lambda_{i,k} \cdot Z_i \quad \text{for all } k$$

where
$\hat{Z}_k$ = is the interpolated value at grid location "k".
$\lambda_{i,k}$ = is the weight associated with electrode measurement "i" when estimating grid location "k".
$Z_i$ = known electrode measurement "i".

The weights used to interpolate the value at grid location "k" are unique to grid location "k"; that is, a different set of weights must be calculated for every grid location. The weights used to interpolate the value at grid location "k" are functions of the various separation distances between pairs of the 15 known electrode measurements, and the various separation distances between the 15 known electrode measurements and the grid location "k".

The weights are generated by solving the following set of 16 linear equations involving 16 unknowns. The 16 unknowns are comprised of the 15 weights plus a "lagrange multiplier". This last term the lagrange multiplier) is included for mathematical convenience and is not used in the computation of the interpolated value.

The Kriging weights for interpolating the value at grid location "k" are generated by solving, in the equivalent matrix form, the following system of linear equations:

$$\begin{bmatrix} 1.8 & 1.8 & & 1.8 \\ d_{1,1} & d_{1,2} & \cdots & d_{1,15} & 1 \\ d_{2,1}^{1.8} & d_{2,2}^{1.8} & & & \\ & & d_{ij}^{1.8} & & \\ & & & & \\ d_{15,1}^{1.8} & & & d_{15,15}^{1.8} & 1 \\ 1 & 1 & \cdots & 1 & 0 \end{bmatrix} \begin{bmatrix} \lambda_1 \\ \lambda_2 \\ \cdot \\ \cdot \\ \cdot \\ \lambda_{15} \\ \mu \end{bmatrix} = \begin{bmatrix} 1.8 \\ d_{1,0} \\ d_{2,0}^{1.8} \\ \cdot \\ \cdot \\ d_{15,0}^{1.8} \\ 1 \end{bmatrix}$$

where $d_{ij}$ = the distance between electrode "i" and electrode "j".

$\lambda_i$ = weight associated with electrode "i".

$\mu$ = lagrange multiplier.

$d_{io}$ = the distance between electrode "i" and the grid location.

The various equations described above are found derived in various publications in geostatistics including a book entitled "Random Functions and Hydrology" pps. 385–412 by R. L. Bras and I. Rodriguez-Iturbe-Addison Wesley Publishing Co., Reading, Mass. and in a book entitled "Mining Geostatistics" Academic Press, N.Y. (1978) by A. G. Journel and Ch. J. Juijbregts. Similar sets of equations and their matrix equivalents for the more general universal kriging can be found in these same references.

Once a set of weights has been derived for a given configuration of electrodes, this set of weights can be used for any subsequent Kriging interpolation from the same electrode configuration with substantial increase in efficiency.

In FIG. 1, as a close subset of the International 10–20 Convention there are shown the sites of the fifteen electrodes, distributed as indicated on the outline of the head shown by the solid circle. The electrodes are shown associated with the rectangle overlying the circle, and this rectangle essentially corresponds to a flattening of the scalp surface of interest. Based on the voltages measured at each of these electrodes, Kriging interpolation in the manner described above is used to derive the three dimensional contoured potential surface, shown in FIG. 2, for the portion of the head included within the rectangle, viewed from the rear, above and slightly to the right of the dotted midline shown in FIG. 1.

A reference electrode, not shown, would be placed in a relatively inactive area, for example, the back of the head. The exact position of the individual recording electrodes is not critical and is generally dictated by the task being evaluated and by experience, although it is advantageous to locate electrodes over regions where current generation is expected. Moreover, the particular number, 15, is not critical though found a reasonable compromise between sufficient samples for a good estimation and the complexity increase as the number of samples is increased.

In other tasks, a different number of electrodes may represent a better compromise. The invention should prove useful even when as few as four recording electrodes are used for the particular task in mind.

To achieve the surface depicted, Kriging using a variogram to the 1.8 power, as discussed above, is used to define a rectangular two-dimensional grid of 63 points by 23 points, each corresponding to X and Y coordinates of interest and for each grid point there is provided a potential value. There is provided such a grid for each complete set of potential points measured at a given time. Typically, 128 such grids for 128 sets have been calculated, spaced apart in time one sampling interval, typically 6.24 milliseconds, corresponding to an analysis time of about 800 milliseconds for a complete cycle or epoch.

Figure 2:
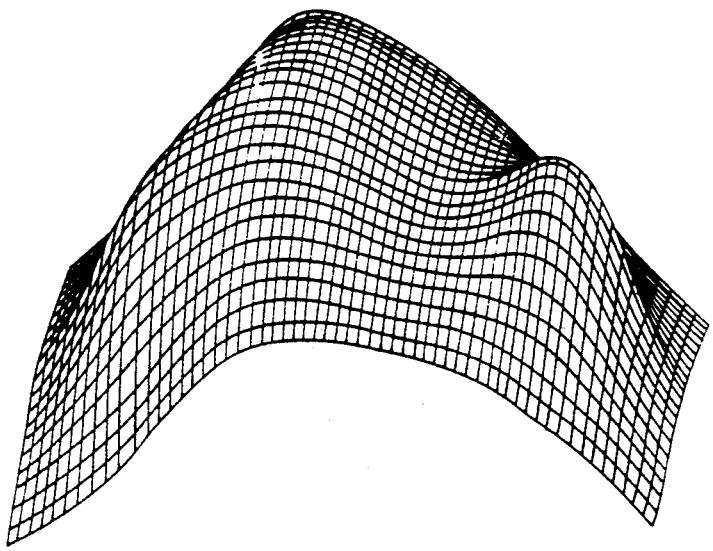
FIG. 2 shows a three-dimensional event-related-potential surface derived from fifteen originally measured points after Kriging interpolation, as is characteristic of a typical embodiment of the data processing technique of the invention.

To facilitate the ease of observation, the two dimensional grid of points, each of an appropriate magnitude, is transformed to a three dimensional contoured surface of the kind shown in FIG. 2 by techniques now familiar in image processing for special effects, in which the third z dimension, or height, represents the voltage at the point having the corresponding X and Y coordinates. The image processing technique is used to provide a perspective view.

More particularly, FIG. 2 shows a plot of the potential surface resulting from one such grid of 63 points by 23 points. In particular, it is to be noted that the potential surface is relatively smoothly varying and passes through all of the measured points available with good support between points, as is needed to provide, after the Laplacian transformation, a surface of current density consistent with what is expected from established measuring techniques.

This is in contrast to the interpolation by distance-weighted average techniques which results in products in which most data points considered show up as local maxima or spikes.

Figure 3:
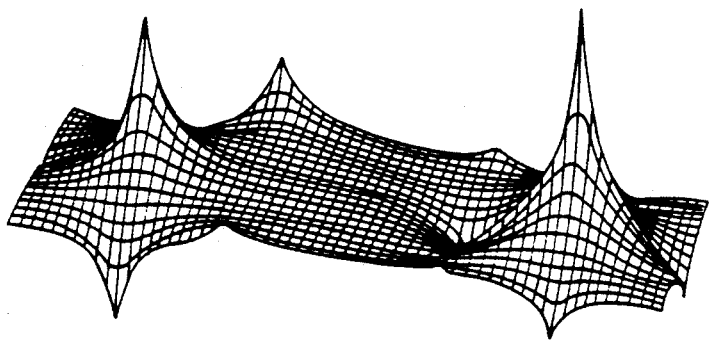
FIG. 3 illustrates the three-dimensional Laplacian current density surface derived from the potential surface shown in FIG. 2 in the manner characteristic of the invention.

The evoked potential data depicted in FIG. 2 is now further processed by a five point differential operator to obtain a "Laplacian map". The Laplacian map provides a direct estimate of the magnitude of current flowing perpendicular to the surface of the scalp and thus, the distribution of currents passing into and out of the brain at each point in space. In FIG. 3 there is shown the Laplacian current topography approximating the second spatial derivative of the interpolated potential surface shown in FIG. 2. As can be seen from comparison of the potential and current flow topographies shown in the two figures, the Laplacian mapping provides a sharper spatial resolution of the current flow features, since the elimination of potential gradients due to tangential extracranial current flow permits the localization of those portions of the extracranial currents attributable to generators within the brain. In particular, it is to be noted that the Laplacian mapping highlights features of interest not immediately obvious from the potential surface and significantly eases the problem of distinguishing the features of interest. Transcranial current flow maxima can be readily identified visually from a live computer cartoon-type sequential display of the spatiotemporal mappings. This defines the location and timing of peak current flows for concentrated study.

The amplitude and latency of each peak may be employed as the measures of timing and magnitude of processing within a particular brain region. Topographic data obtained from infants and adults has permitted the delineation of two major intracranial generators of the auditory evoked related potentials that correspond to peaks in the ERP topography, one located within the superior temporal plane projecting fields toward the paramedian frontocentral scalp, and another within the lateral surface of the superior temporal gyrus that projects to the immediately overlying temporal scalp illustrated in FIG. 3.

Data from auditory processing tasks that require both acoustic and semantic analysis indicates the presence of a third, more posterior generator that is active during semantic processing. Thus, four distinct current maxima, two from each hemisphere, are present when acoustic processes alone are activated, whereas additional maxima may be present when semantic processing is required. Should the Laplacian of more complex linguistic tasks provide evidence for further differentiation of regional cortical generators, these additional current maxima can also be measured in the same manner as described.

In tests which have been conducted, the improved spatial resolution provided by Laplacian analysis has increased the validity of peak amplitude measurements, since spatial overlap of field distributions from adjacent intracranial generators is reduced. The proposed method of peak identification and measurement also substantially reduces the number of quantitative variables required to define the spatiotemporal event-related-potential distributions, and increases the power of statistical comparisons.

The specific results depicted involved ordinary Kriging. As mentioned above, universal Kriging can provide improved interpolation when more measured data points are available and/or when there can be used knowledge of the underlying neural activity. Universal Kriging permits the incorporation of knowledge about electric potential fields and about human and animal electrophysiology into the expressions for the variogram and the deterministic trend term characteristic of universal Kriging as discussed previously.

Definition of the timing of each current maximum has permitted confirmation of inferences on the role of the underlying neural activity in stimulus information processing. Thus, for example, potentials that reflect acoustic processing precede those associated with semantic processes and arise from different brain regions. Further, peaks whose latency exceeds that of a behavioral response can be excluded from consideration as manifestations of the discriminative process.

For use by a clinician, the process described typically would be employed for each of the 128 sampling intervals to provide a set of 128 frames each showing a Laplacian surface of the kind shown for the particular sampling interval. It is feasible to use the same set of weights, originally derived for the first frame, for the remaining frames. If each of these frames is displayed in turn on a television monitor at an appropriate rate, there is achieved a cartoon-like moving display of the Laplacian surface with the peaks shown rising and falling to simulate the spatial pattern of focal current generation changes through time.

It is, of course, desirable to compare visually such changes of an individual case under study with a norm to detect any dysfunction. To this end, there is again derived 128 grids, each including 63 points by 23 points in which the magnitude of each point is derived as the grand mean of a cohort of normal cases, typically at least fifteen, derived in the manner described and from these grids there are also derived 128 frames of Laplacian surface of the kind shown in FIG. 3. Thereafter, either in a separate television monitor or in a separate window in a multiwindow monitor the two cartoon-like displays can be viewed in synchronism side by side for comparison.

Moreover, in some instances it will be desirable to display in the same way simultaneously the z- score of corresponding points in an individual case grid where in the usual fashion the z score of a point in the z grid is defined as the magnitude at that point in the Laplacian grid of the individual case minus the magnitude at that point in the Laplacian mean grid, divided by the standard deviation calculated in the usual fashion for that point in the standard deviation grid calculated from the distribution of normal case Laplacian grids. In this way there may be simultaneously displayed a surface in which the elevation of a point in the surface corresponds to the z-score of that point in the scalp at its particular time frame.

In familiar fashion, provision can be included for freezing a time frame of the displays for closer inspection or for slowing or speeding of the rate of change of the potential at the scalp. In particular, it is possible to collect from each of the 128 sampling intervals both the potential value and the current density (Laplacian) value at a particular point of the surface, for example, a point corresponding to the location of any selected one of the fifteen electrodes used for taking the potential measurements, and these values may be plotted against time for displaying the change with time of the potential value and the current density at the selected points.

Figure 4:
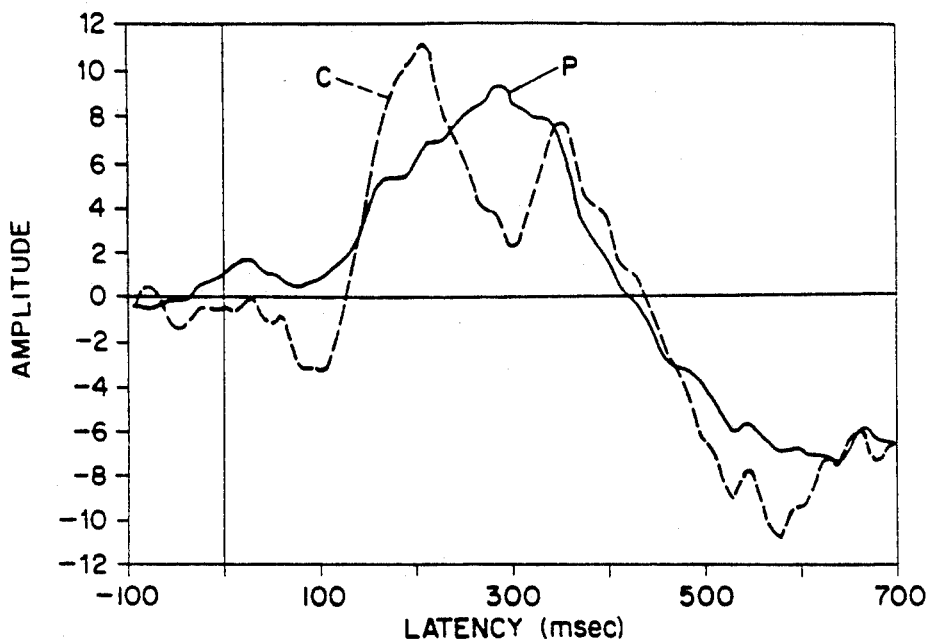
FIG. 4 is a plot against time of both the potential and the current density at a particular point that can readily be derived from the data shown in FIGS. 2 and 3.

In FIG. 4, which is such a display, there are shown temporal waveforms at electrode C3M of the current density C and of the original potential P. It will be noted that the current density waveform C highlights features not readily discerned in the original potential waveform P. Such a representation is of particular value as an analytical tool to the investigator, because it is a concise summary of the parameters of interest.

Figure 5:
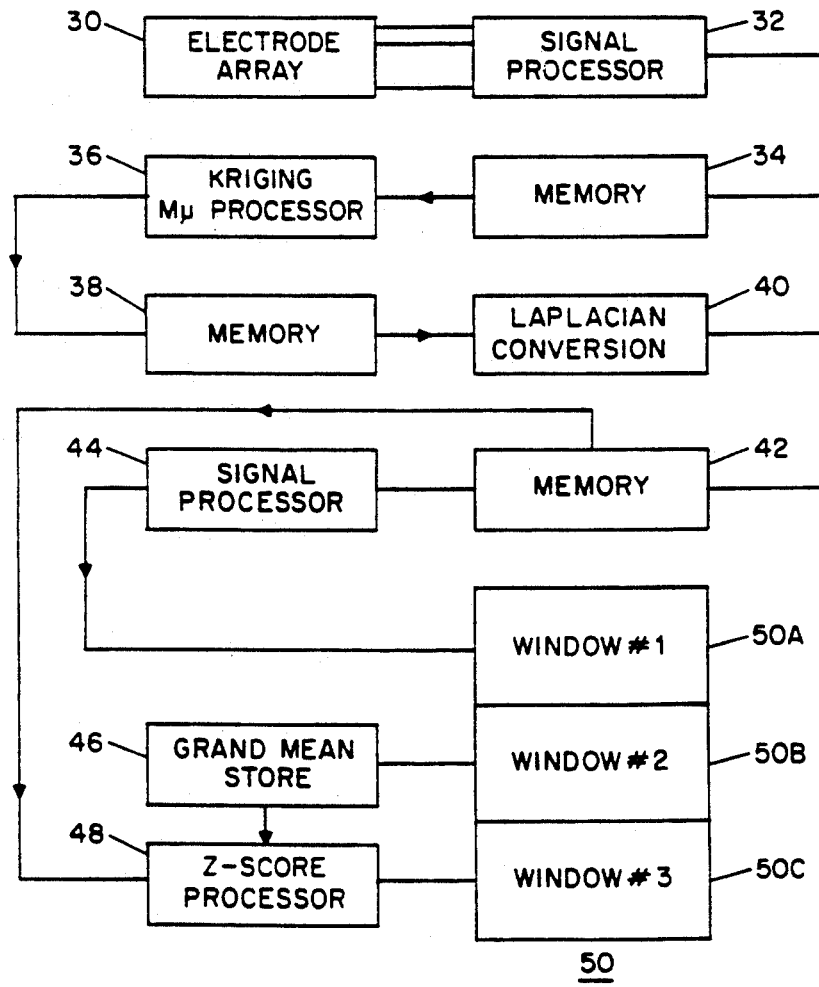
FIG. 5 is a block schematic of apparatus for use in an illustrative embodiment of the invention.

In FIG. 5, there is shown in block schematic form the basic elements of apparatus suitable for carrying out the processing described.

The first block 30 included represents the electrode array positioned appropriately in the area under study. In humans, this typically will be on the skin surface. In animals, these may also be in an interior area.

The signals derived by the electrodes typically are very weak and so are first amplified before further processing. It is then usually advantageous to sample the individual continuous wave analog signals from each electrode, typically into 128 samples, for the time expected for one epoch of the evoked potential wave in the area under study and each sample is digitized in binary code. Since the signals are not usually processed in real time, the various digitized samples of the various electrodes will be stored in sequence in a suitable storage medium, either a tape or disk. Typically, the stimulus will be repeated a number of times and the average of the successive values for an individual electrode used in the usual fashion to reduce the signal to noise ratio, based on the fact that random noise will average out while the signal will build up cumulatively. This processing is represented by the signal processor block 32 shown supplied by the leads from the various electrodes of array 30.

The output of the signal processor 32 is shown supplied to a memory 34 where the digitized samples at each electrode for each sampling interval are stored for access when desired. The output of the memory as needed is supplied to a microprocessor 36 programmed to do the Kriging of the digitized samples derived from the fifteen electrodes into a grid of 63 points by 23 points as described, extra points being provided as previously discussed to compensate for edge points to be lost. Generally, it will be desirable to store the values of 128 grids, corresponding to one for each of the 128 sampling intervals, in a memory 38 as depicted.

The various grid values are supplied as needed from the memory 38 to a microprocessor 40 programmed to do the five point differential Laplacian conversion, previously discussed, to derive for each of the 128 grids a corresponding grid each of 61 points by 21 points, assuming provision has been made for the extra points being lost, as discussed above. Essentially, the five point differential operation amounts to taking the average of the sum of four differences, each corresponding to the difference of the value at a center point from the value at each of four proximate surrounding points. The four points may comprise the two points on the same horizontal line on opposite sides of the point being interpolated plus the two points on the same vertical line on opposite sides of the point being interpolated. Alternatively, the points may be the four closest points around the central point on diagonals through the central point. There is then similarly stored the values of 128 grids, one for each sampling interval in a memory 42 for use as needed in the signal processor 44, which uses the signals stored in memory 42 to develop for each of a 128 grids of values a grid of values that can be scanned to produce, in perspective, a surface of the kind depicted in FIG. 3.

Of course other number and arrangements of points can be used for the Laplacian derivation, as is familiar to workers in the art.

The output of the signal processor 44 along with the grids of the grand means stored in store 46 and the Z-scores calculated in signal processor 48 are supplied, appropriately synchronized, to three separate windows 50A, 50B and 50C of the screen monitor 50. The z-score processor 48 also needs to be supplied with information about the Laplacian grids of the individual case, available from memory 42, and information about the grand mean Laplacian grids, available from store 46.

Additionally, for a display as shown in FIG. 4; there can be derived from memory for any particular point of the grid the values of potential and current density for each successive sampling interval.

It can be appreciated that various modifications can be made in the basic system described without departing from the spirit and scope of the invention. In particular, the Kriging technique can be used to interpolate any desired number of points between two given points. It is generally important for a marked advantage in the subsequent Laplacian derivation to obtain at least about a tenfold increase in the total number of points, corresponding to about a threefold increase in each of the x and y dimensions. However, obviously any increase in the number of points can effect an improvement and there may be instances where a smaller increase will suffice.

Moreover, as was previously indicated, the specific process described can be used for mapping the current density distribution in various other parts of the body. Generally, each such task will involve the placement of a suitable number of electrodes in appropriate positions related to the task. As a consequence, other forms of variograms may be preferred for the Kriging.

By the use of this technique, together with appropriate positioning of particular electrodes to emphasize particular electrophysiologic responses, there can be derived a wide variety of data to pinpoint the timing and locus of underlying neural activity.

There accordingly will be provided a better means for directly identifying the presence and spatiotemporal characteristics of electrophysiological activity in individual subjects.

I claim:

1. A process for deriving the current density at points over an area of interest as a measure of the underlying neural activity comprising:
   the step of measuring physiological potentials at a limited number of points over the area of interest by means of electrodes to yield electrical signals indicative thereof;
   the step of using the electrical signals to estimate the potential at each of an increased number of points over the area of interest by Kriging interpolation of the measured potentials; and
   the step of deriving from said estimated potentials a current density value at each of said points.

2. The process of claim 1 in which the Kriging interpolation is ordinary Kriging.

3. The process of claim 1 in which the Kriging interpolation is ordinary Kriging with a power function variogram model.

4. The process of claim 3 in which the variogram is used with a power function raised to between 1.4 and 1.8.

5. The process of claim 1 in which the Kriging interpolation is universal Kriging utilizing information available as to the underlying neural activity in the area of interest.

6. The process of claim 1 wherein the step of Kriging interpolation and the step of deriving current density values are calculated in a single step.

7. The process of claim 6 wherein the single step is performed by a microprocessor.

8. The process of claim 1 wherein the estimating step and the deriving step is performed by a microprocessor.

9. The process of each of claims 1, 2, 3, 4, and 5 in which the current density is calculated from a Laplacian transformation of said estimated point potentials.

10. The process of each of claims 1, 2, 3, 4 and 5 in which the step of deriving the current density involves a five point difference operator to approximate a second spatial derivative at each point.

11. The process of each of claims 1, 2, 3, 4, and 5 in which said Kriging interpolation generates at least about a five fold increase in the number of points.

12. Apparatus for displaying the features of underlying neural activity over an area of interest comprising:
   means for measuring physiological potentials at a plurality of points and for generating electrical signals indicative thereof;
   a first electronic means for processing said signals to derive a grid of estimated potential values, corresponding to the area of interest, of increased density by a Kriging interpolation program;

a second means for processing said grid of estimated potential values to derive a corresponding grid of current density values; and means for displaying in perspective a three dimensional image representing said grid of current density values and displaying thereby the current density features of underlying neural activity over the area of interest.

13. The apparatus of claim 12 in which the electronic means for processing said grid of estimated potential values uses a Laplacian transformation to derive a corresponding grid of current density values.

14. The apparatus of claim 12 in which the electronic means for processing said grid of estimated potential values uses a five point difference operator to derive a corresponding grid of current density values.

15. The apparatus of claim 12 in which the interpolation is ordinary Kriging.

16. The apparatus of claim 12 in which the interpolation is universal Kriging.

17. The apparatus of claim 12 in which the Kriging interpolation is ordinary Kriging with a power function variogram model.

18. The apparatus of claim 17 in which the variogram is used with a power function raised to between 1.4 and 1.8.

19. Apparatus for displaying features of underlying neural activity over an area of interest comprising:

an electrode array positioned over the area of interest for measuring potentials at a corresponding number of points over such area and means for generating electrical signals indicative thereof;

signal processing means for providing interpolated values by a Kriging interpolation program of potentials at points intermediate between said corresponding numbers of points for providing an increased number of potential values;

signal processing means for deriving a substantially corresponding number of current density values for the area of interest; and means for displaying the current density values as a perspective three dimensional display of the current density values over the area of interest.

20. Apparatus in accordance with claim 19 in which said Kriging program utilizes ordinary Kriging.

21. Apparatus in accordance with claim 19 in which said Kriging program is a universal Kriging interpolation.

22. The apparatus of claim 19 in which the Kriging interpolation is ordinary Kriging with a power function variogram.

23. The apparatus in accordance with claim 22 in which the variogram is used with a power function raised to between 1.4 and 1.8.

24. The apparatus of claim 19 in which the Kriging interpolation is universal Kriging.

25. The apparatus of claim 19 in which the signal processing means derives the current density by performing a Laplacian transformation.

26. The apparatus of claim 19 in which the signal processing means derives the current density by using a five point difference operator.

27. Apparatus for displaying features of underlying neural activity at a desired point in an area of interest on a human or animal comprising:

a plurality of electrodes for positioning at points over the area of interest and means for deriving therefrom electrical signals as measures of the physiological potentials at such points;

a first electronic means to derive by a Kriging interpolation program a grid of estimated potential values of an area corresponding to the area of interest with a greater coordinate density than the number of original points;

a second electronic means for processing said grid of estimated potential values to derive a corresponding grid of current density values;

means for sampling the values of a selected point in the grid of estimated potential values and the grid of current density values corresponding to the desired point; and means for displaying said sampled values of the estimated potential and of the current density at the desired point in successive sampling intervals in a plot against time.

28. Apparatus in accordance with claim 27 in which the plurality comprises fifteen electrodes.

29. The apparatus of claim 27 in which the Kriging interpolation is ordinary Kriging.

30. The apparatus of claim 27 in which the Kriging interpolation is ordinary Kriging with a power function variogram model.

31. The apparatus of claim 30 in which the variogram is used with a power function raised to between 1.4 and 1.8.

32. The apparatus of claim 27 in which the Kriging interpolation is universal Kriging.

33. The apparatus of claim 27 in which the signal processing means derives the current density by performing a Laplacian transformation of said grid points.

34. The apparatus of claim 27 in which the signal processing means derives the current density by using a five point difference operator to approximate a second spatial derivative at each grid point.

35. Apparatus for displaying features of underlying neural activity over an area of interest of a human or animal body comprising:

means for measuring physiological potentials at a plurality of points and for generating electrical signals indicative thereof;

a first signal processing means for deriving by a Kriging interpolation for the area of interest, potential values at a grid of points of a density greater than the measured points;

a second signal processing means for deriving current density values at said grid of points; and means for displaying the current density values at points in the area of interest.

36. Apparatus in accordance with claim 35 in which the means for displaying current density values at points in the area of interest displays said values at successive sampling intervals whereby there is a dynamic display of the current density values with changing time.

37. The apparatus of claim 35 in which the Kriging interpolation is ordinary Kriging.

38. The apparatus of claim 35 in which the Kriging interpolation is ordinary Kriging with a power function variogram model.

39. The apparatus of claim 38 in which the variogram is used with a power function raised to between 1.4 and 1.8.

40. The apparatus of claim 35 in which the Kriging interpolation is universal Kriging.

41. The apparatus of claim 35 in which the signal processing means derives the current density by performing a Laplacian transformation of said grid points.

42. The apparatus of claim 35 in which the signal processing means derives the current density by using a five point difference operator.

43. The apparatus of claim 35 wherein the first signal processing means and the said second signal processing means comprises a microprocessor.

44. Apparatus for displaying features of underlying neural activity over an area of interest comprising:
- means for measuring physiological potentials at a plurality of points and for generating electrical signals indicative thereof;
- a first electronic means for processing said signals to derive a grid of estimated potential values, corresponding to the area of interest, of increased density by a Kriging interpolation program;
- a second electronic means for processing said grid of estimated potential values to derive a corresponding grid of current density values; and
- means for displaying in perspective a three dimensional image representing said grid of estimated potential values and displaying thereby potential features of underlying neural activity over the area of interest.

45. The apparatus of claim 44 in which the Kriging interpolation is ordinary Kriging.

46. The apparatus of claim 44 in which the Kriging interpolation is ordinary Kriging with a power function variogram model.

47. The apparatus of claim 46 in which the variogram is used with a power function raised to between 1.4 and 1.8.

48. The apparatus of claim 44 in which the Kriging interpolation is universal Kriging.

49. The apparatus of claim 44 in which the signal processing means derives the current density by performing a Laplacian transformation of said grid points.

50. The apparatus of claim 44 in which the signal processing means derives the current density by using a five point difference operator.

51. The apparatus of claim 12, 27 or 44 wherein the said first electronic means for deriving a grid of estimated potential values and the said second electronic means for deriving said grid of current density values comprises a microprocessor.

* * * * *

UNITED STATES PATENT AND TRADEMARK OFFICE
CERTIFICATE OF CORRECTION

PATENT NO. : 5,247,436

DATED : September 21, 1993

INVENTOR(S) : Charles L. Stone, Jr.

It is certified that error appears in the above-identified patent and that said Letters Patent is hereby corrected as shown below:

Title page, Item 56, 10th line, "David, Michael" should read David, Michel--;

Title page, 2nd col., 4th line, "Probalility" should read --Probability--;

Col. 7, line 31, "term the" should read --term (the--; and

Col. 17, line 7, "claim 35" should read --claim 19 or 35--.

Signed and Sealed this

Thirty-first Day of May, 1994

Attest:

BRUCE LEHMAN

Attesting Officer    Commissioner of Patents and Trademarks